US006994091B2

(12) United States Patent
Griesbach, III

(10) Patent No.: US 6,994,091 B2
(45) Date of Patent: Feb. 7, 2006

(54) SURGICAL DRAPE WITH DIVERTING FEATURE

(75) Inventor: Henry L. Griesbach, III, Clarkston, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 269 days.

(21) Appl. No.: 10/326,913

(22) Filed: Dec. 20, 2002

(65) Prior Publication Data

US 2004/0118409 A1    Jun. 24, 2004

(51) Int. Cl.
*A61B 19/00* (2006.01)
(52) U.S. Cl. ...................................... 128/849; 128/853
(58) Field of Classification Search ......... 128/849–856
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,855,046 A | 12/1974 | Hansen et al. | |
| 3,921,627 A * | 11/1975 | Wilson et al. | 128/853 |
| 4,134,398 A * | 1/1979 | Scrivens | 128/852 |
| 4,169,472 A * | 10/1979 | Morris | 128/854 |
| 4,340,563 A | 7/1982 | Appel et al. | |
| 4,379,192 A | 4/1983 | Wahlquist et al. | |
| 4,873,997 A * | 10/1989 | Marshall | 128/849 |
| 5,140,996 A | 8/1992 | Sommers et al. | |
| 5,151,314 A | 9/1992 | Brown | |
| 5,258,221 A | 11/1993 | Meirowitz et al. | |
| 5,464,024 A | 11/1995 | Mills et al. | |
| 5,540,979 A | 7/1996 | Yahiaoui et al. | |
| 5,832,927 A * | 11/1998 | Wijesinghe et al. | 128/849 |
| 5,975,082 A | 11/1999 | Dowdy | |
| 6,055,987 A | 5/2000 | Griesbach et al. | |
| 6,314,959 B1 | 11/2001 | Griesbach et al. | |
| 2002/0177826 A1 | 11/2002 | Davis et al. | |

FOREIGN PATENT DOCUMENTS

WO     WO 0241800     5/2002

OTHER PUBLICATIONS

International Search Report, Apr. 19, 2004.
U.S. Appl. No. Unknown, Titled "Surgical Drape Having an Instrument Holder", filed Dec. 18, 2002.

* cited by examiner

*Primary Examiner*—Michael A. Brown
(74) *Attorney, Agent, or Firm*—Dority & Manning

(57) ABSTRACT

A surgical drape for use during surgery of a patient is provided. The surgical drape includes a sheet that is configured for covering at least a portion of the patient during surgery. At least one diverting feature is located on the sheet, and has substantially the same fluid absorbent properties as a section of the sheet that is immediately adjacent to the diverting feature. The diverting feature is configured for at least partially transferring fluid from one location on the sheet to another location on the sheet.

31 Claims, 17 Drawing Sheets

| Sample No. | Description / Embossing Condition | Unembossed Regions, mm | Embossed Region A, mm | Embossed Region B, mm | Embossed Region C, mm |
|---|---|---|---|---|---|
| 1 | Fabric / SB facing Embossing Plate, 57.2° C for 5 min. | 0.509 | 0.356 | 0.308 | .347 |
| 2 | Film / from Fabric 1 | 0.0455 | 0.033 | --- | --- |
| 3 | Fabric / SB facing Embossing Plate, 61.66° C for 5 min. | 0.457 | 0.288 | 0.299 | .322 |

FIG.2

| Sample No. | Description / Embossing Condition | Unembossed Regions, mm | Embossed Regions, mm | Thickness Change from Embossing, % |
|---|---|---|---|---|
| 4 | Fabric / SB facing Embossing Plate, 1.91 cm Foam | 0.528 ± 0.012 | 0.284 ± 0.015 | 46 |
| 5 | Fabric / SB facing Embossing Plate, 2.86 cm Foam | 0.536 ± 0.018 | 0.271 ± 0.045 | 49 |
| 6 | Fabric / Film facing Embossing Plate, 1.91 cm Foam | 0.500 ± 0.016 | 0.338 ± 0.053 | 32 |
| 7 | Fabric / Film facing Embossing Plate, 2.86 cm Foam | 0.541 ± 0.041 | 0.330 ± 0.020 | 39 |

FIG.3

| Sample No. | Description | Thickness | % Absorbency |
|---|---|---|---|
| 5 | Embossed Region | 0.271 ± 0.045 | 214 ± 12 |
| 7 | Embossed Region | 0.330 ± 0.020 | 279 ± 11 |
| 4 | Unembossed Fabric | 0.528 ± 0.012 | 393 ± 10 |
| 5 | Unembossed Fabric | 0.536 ± 0.018 | 390 ± 6 |
| 6 | Unembossed Fabric | 0.500 ± 0.016 | 383 ± 4 |
| 7 | Unembossed Fabric | 0.541 ± 0.041 | 385 ± 8 |

FIG.4

| Sample Series | Description | Normalized Runoffs At Angles: | | | | Embossed Thickness, mm |
|---|---|---|---|---|---|---|
| | | 15° | 25° | 35° | 45° | |
| 8 | Edge embossed 5 ridges | 0.49 | 0.82 | | 1.11 | 0.27 |
| 9 | Edge embossed 5 ridges | | 0.84 | 0.99 | 1.04 | 0.27 |
| 10 | Partial Embossed 2 ridges | | 0.80 | | | 0.30 |
| 11 | Partial Embossed 3 ridges | | 0.74 | | | 0.31 |
| 12 | Densified | | 0.81 | | 0.96 | 0.40 |
| 13 | Embossed Up 10.16 cm from edge | | 0.88 | 1.06 | 1.01 | 0.27 |
| 14 | Edge embossed Film Up | | 0.95 | | | 0.33 |
| 15 | Edge embossed Reversed | | 0.92 | 0.94 | 1.02 | 0.28 |
| 16 | Control (no embossing) | | 1.03 | | 0.84 | 0.49 |

FIG.6

| Repetition | Sample Weight, gm | Run-Off, gm | Normalized Run-off | Embossed Thickness, mm |
|---|---|---|---|---|
| 1 | 8.36 | 7.66 | 0.92 | 0.32 |
| 2 | 8.25 | 6.34 | 0.77 | 0.25 |
| 3 | 8.35 | 5.25 | 0.63 | 0.27 |
| 4 | 8.30 | 8.06 | 0.97 | 0.27 |
| Average | 8.32 | 6.82 | 0.82 | 0.28 |

FIG.7

SURGICAL DRAPE WITH DIVERTING FEATURE

BACKGROUND

Various types of surgical drapes have been used to keep a surgical site on a patient sterile during a surgical procedure. Traditionally, surgical drapes were linen or woven cloth, and were sterilized after each use for reuse. More recently, disposable drapes have been introduced, in which a nonwoven paper or fabric forms a substantial part of the drape. A reinforcement area is often placed around a fenestration or an edge of disposable surgical drapes to provide structural strength and to absorb bodily fluids from a surgical site. Many disposable drapes also include a number of layers of different materials for the drape area and reinforcement area, with each layer providing a different property to the drape. For example, spunbond fabrics, meltblown fabrics, and polymer films have been used as layers in disposable drapes.

Many different shapes of surgical drapes have been proposed, often depending upon the specific surgical procedure to be performed. For example, the shape of the drape is often specifically designed to fit around a specific surgical site on the body. In some cases, a fenestration, as mentioned above, is provided through a drape to allow medical personnel access to the surgical site, whereas the remaining sheet portion of the drape covers the rest of the body and table. Moreover, several drapes are often used in combination to cover a patient. In some cases, several rectangular drapes, often called universal drapes, are laid over the patient in a pattern providing an opening through which the medical personnel can access the surgical site while also covering the remainder of the patient's body and the table.

Certain surgical procedures involve large amounts of fluid, for example blood or saline irrigation fluid, at the point of surgery. Certain procedures also require the fluid to be removed from the point of surgery and safely contained within a container or absorbent material. For instance, towels or other absorbent material that is placed on the top surface of a surgical drape may be used to absorb this fluid. It is also the case that suctioning devices and surgical sponges are used to remove fluid that is within the patient during the surgical procedure.

Problems with the towels and other absorbent material placed around the point of surgery exist where the towel or absorbent material becomes so saturated with fluid that the fluid begins to wet the patient, clinician, and/or surgical table. As such, drapes have been provided with features that are designed to transport fluid away from the point of surgery to another point on the surgical drape where the fluid can be absorbed or removed. This is done in order to move the fluid from a zone proximate to the point of surgery to another location on the surgical drape that will reduce the likelihood of contamination to and from the patient and clinician. Drapes with a plastic trough attached to the surgical drape and positioned so as to transport fluid from the point of surgery to a more remote area of the surgical drape are examples of one way that such features are provided.

Also, these types of draining features have been made of the same absorbent material used in a surgical drape, but treated so as to be of lesser absorbency than the absorbent material into which the trough drains. In this instance, the trough is made by heat treating a particular absorbent material so that the portion of the absorbent material formed into the trough is of a lesser absorbency than the absorbent material into which the trough drains. However, these types of drainage features on surgical drapes are limited in that they are only capable of transferring fluid from one location on the drape to another location. In essence, the drainage features of present surgical drapes do not provide for a way of spreading the fluid out over a larger portion of the absorbent material so that the fluid is more readily and safely absorbed. Current drainage features on surgical drapes are only capable of transporting fluid from one location to another, and as such still allow a particular portion of the surgical drape to become saturated with fluid and hence increase the probability of the fluid leaking from the surgical drape and not being properly absorbed.

As such, a need currently exists for a surgical drape that has a diverting feature for fluid that both diverts the flow of fluid on the surgical drape and provides for a better absorption scheme on the surgical drape.

SUMMARY

Various features and advantages of the invention will be set forth in part in the following description, or may be obvious from the description, or may be learned from practice of the invention.

A surgical drape for use during surgery of a patient is provided. The surgical drape includes a sheet that is configured for covering at least a portion of the patent during surgery. At least one diverting feature is located on the sheet. The diverting feature has substantially the same fluid absorbent properties as a section of the sheet immediately adjacent to the diverting feature. The diverting feature is configured for at least partially transferring fluid from one location on the sheet to another location while absorbing at least a portion of the fluid.

Also, in another exemplary embodiment of the present invention, the sheet may have an absorbent region and the diverting feature may be located in the absorbent region. The diverting feature may be integrally formed with the absorbent region.

In certain exemplary embodiments of the present invention, the diverting feature may be a plurality of channels that are made of the same material as the absorbent region. The channels are of a higher density than the remainder of the absorbent region. The diverting feature may be formed on the surgical drape by a variety of manufacturing processes. For instance, the diverting feature may be embossed on the absorbent region. The diverting feature may also be located in various orientations with respect to one another and the sheet. For instance, the diverting feature may be a plurality of channels that are spaced apart from and parallel to one another in one exemplary embodiment to the present invention. Also, a further exemplary embodiment of the present invention exists where the channels have the same width.

In accordance with another exemplary embodiment of the present invention, the sheet of the surgical drape may have a fenestration where the diverting feature is spaced from and surrounds the fenestration.

Also, the diverting feature may be channels that have an elongated portion and a narrow portion. The direction of the elongated portion is perpendicular to the direction of fluid flow induced by gravity on the absorbent region.

The present invention also provides for in one exemplary embodiment a method for forming the diverting feature in the surgical drape. The method includes positioning the drape between an embossing plate and a resilient member, which in a further exemplary embodiment may be a high temperature resistant rubber deformable foam. The method further includes the step of applying a force so that the embossing plate engages the drape and at least a portion of the drape is urged into the resilient member. The drape is then heated while being urged into the resilient member. Also, the drape is removed from the resilient member and the diverting feature is formed on the drape.

Other features and aspects of the present invention are discussed in greater detail below.

BRIEF DESCRIPTION OF THE DRAWINGS

FIG. 2 is a table showing thickness values as the average values of at least three repetitions of thickness regions in drapes having a diverting feature in accordance with the present invention.

FIG. 3 is a table showing thickness values and percentage change in thickness due to embossing conditions.

FIG. 4 is a table showing the percentage absorbency of various absorbent regions of drapes.

FIG. 6 is a table showing the normalized run-off of samples of absorbent drape fabric with and without diverting features positioned at different angles during a modified run off test.

FIG. 7 is a table showing the individual measurements and the resulting average used for sample series 8 in the table of FIG. 6 at an inclined angle of 25°.

DETAILED DESCRIPTION

Figure 1:
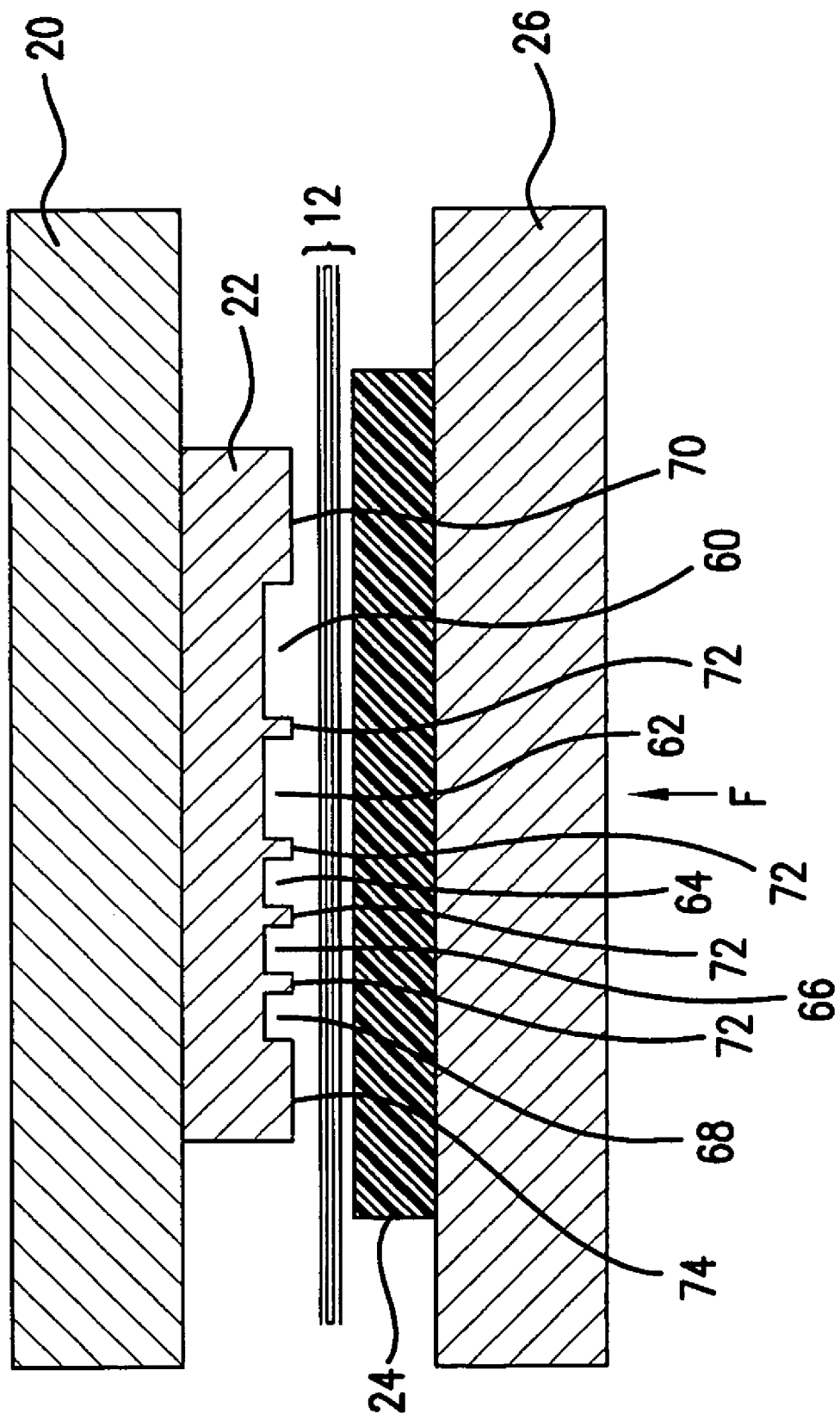
FIG. 1 is a cross sectional view of an arrangement that may be used to make a diverting feature in a drape in accordance with the present invention.

As used herein, the terms "nonwoven web" or "nonwoven" refers to a web having a structure of individual fibers or threads which are interlaid, but not in an identifiable manner as in a knitted fabric. Nonwoven webs or fabrics have been formed from many processes, such as, for example, meltblowing processes, spunbonding processes, and bonded carded web processes. The basis weight of nonwoven fabrics is usually expressed in ounces of material per square yard (osy) or grams per square meter (gsm) and the fibers diameters are usually expressed in microns. (Note that to convert from osy to gsm, multiply osy by 33.91).

As used herein, the term "fiber" generally refers to an elongated strand of defined length, such as staple fibers formed by cutting a continuous strand into lengths of, for example, 2 to 5 cm. Collections of fibers may have the same or different lengths.

As used herein, the term "filament" refers to a generally continuous strand that has a large ratio of length to diameter, such as, for example, a ratio of 1000 or more.

As used herein, "meltblown fibers" refers to fibers formed by extruding a molten thermoplastic material through a plurality of fine, usually circular, die capillaries as molten threads or filaments into converging high velocity, usually hot gas (e.g., air) streams which attenuate the filaments of thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al.

As used herein, "spunbond filaments" refer to small diameter filaments that are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S.

Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond filaments are generally not tacky when they are deposited on a collecting surface.

As used herein, the phrase "thermal point bonding" generally refers to passing a fabric (e.g., fibrous web or multiple fibrous web layers) to be bonded between a heated calendar roll and an anvil roll. The calendar roll is usually patterned in some way so that the entire fabric is not bonded across its entire surface, and the anvil roll is usually smooth. As a result, various patterns for calendar rolls have been developed for functional as well as aesthetic reasons. One example of a pattern that has points is the Hansen-Pennings or "H&P" pattern with about a 30% bond area with about 31 pins/cm$^2$ as taught in U.S. Pat. No. 3,855,046. The H&P pattern has square point or pin bonding areas. Another typical point bonding pattern is the expanded Hansen-Pennings or "EHP" bond pattern that produces a 15% bond area. Another typical point bonding pattern designated "714" has square pin bonding areas wherein the resulting pattern has a bonded area of about 15%. Other common patterns include a diamond pattern with repeating and slightly offset diamonds with about a 16% bond area and a wire weave pattern looking as the name suggests, e.g. like a window screen, with about an 18% bond area. Typically, the percent bonding area varies from around 10% to around 30% of the area of fabric. As is well known in the art, the point bonding holds the resulting fabric together.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

Surgical drapes formed in accordance with the present invention can generally possess any of a variety of sizes and shapes, depending on the particular use of the drape and on its desired properties. For example, certain surgical drape configurations are described in U.S. Pat. No. 6,055,987 to Griesbach, et al., which is incorporated herein in its entirety by reference thereto for all purposes.

Figure 10:
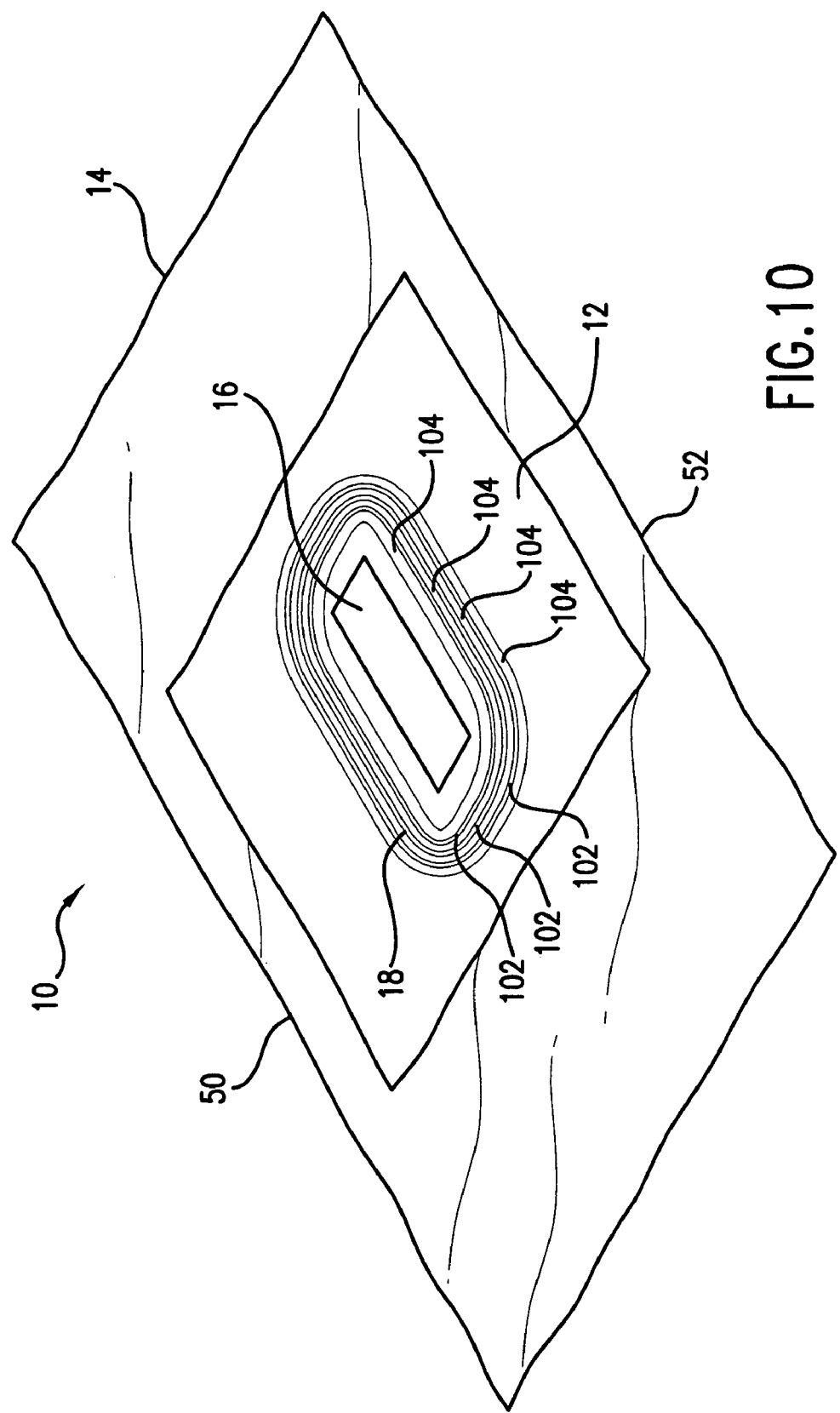
FIG. 10 is a perspective view of an exemplary embodiment of a drape in accordance with the present invention. Here, the diverting feature is shown as being located in the absorbent region of the drape and completely surrounding the fenestration.

Moreover, in one exemplary embodiment, referring to FIG. 10, a surgical drape 10 having a certain configuration is illustrated. In particular, the surgical drape 10 includes a base sheet 14 to which a portion of a fabric 12 is attached. For example, in another embodiment separate from FIG. 10, the drape 10 contains a 193-centimeter×305-centimeter base sheet 14 made of polypropylene spunbond and meltblown layers. Moreover, the fabric 12, in one embodiment, has exterior dimensions of 65 centimeters×100 centimeters.

In some embodiments, such as shown in FIG. 10, at least a portion of the fabric 12 is attached to the base sheet 14 using conventional attachment methods, such as thermal point bonding, point bonding, adhesive, or mechanical bonding. In one embodiment, for example, the fabric 12 can be adhesively laminated to the base sheet 14 using an aqueous adhesive, such as an adhesive sold under the name L 8052-01 by Findley Adhesives.

Figure 14:
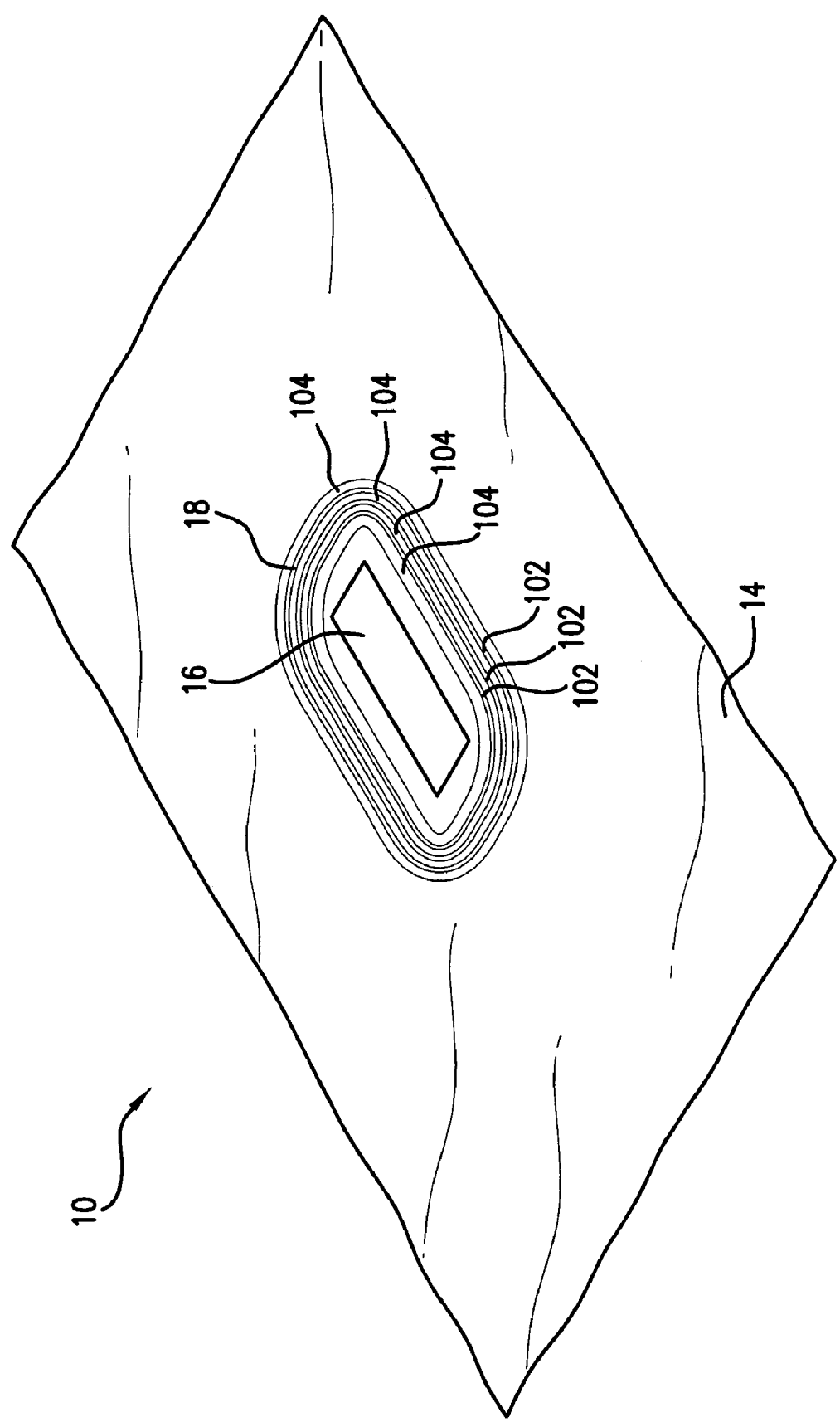
FIG. 14 is a perspective view of an alternative exemplary embodiment of a drape in accordance with the present invention. The drape consists of only one fabric and the diverting feature is included in the drape.

In general, the area of attachment between the fabric 12 and the base sheet 14 can vary. For example, in some embodiments, as shown in FIG. 10, an area less than or equal to the area bounded by the edges 50 and 52 can be bonded to the base sheet 14 using conventional attachment methods. However, as shown in FIG. 14, it should be understood that the fabric 12 is not necessarily required and, if desired, the base sheet 14 may form substantially the entire surgical drape 10. Moreover, as shown in FIG. 19, a fenestration opening is not always required.

As stated, in some embodiments, the drape 10 includes a fenestration opening 16 that can be placed over an operating site during surgery. For example, in one embodiment, a 10-centimeter×30.5-centimeter fenestration opening 16 is provided. In the embodiment depicted in FIG. 10, the fabric 12 also surrounds each side of the fenestration opening 16 so that it may absorb fluids therefrom. However, in some embodiments, the fabric 12 can be placed adjacent to only one, two, or three sides of the fenestration 16.

If desired, the fabric 12 may be constructed so as to have properties that differ from the base sheet 14. For example, large-sized drapes that are intended to completely cover the patient and provide substantial fluid absorption can use a relatively high basis weight, absorbent multilayered nonwoven fabric 12 surrounding the fenestration 16 and include a barrier, such as a film, to inhibit the passage of fluids through the drape 10, while the rest of the drape's base sheet 14 can be relatively low in basis weight The fabric 12 may be used to provide structural support in the area surrounding the fenestration 16. Moreover, as stated above, it should be understood that the surgical drape 10 of the present invention need not contain a separate base sheet 14.

Figure 19:
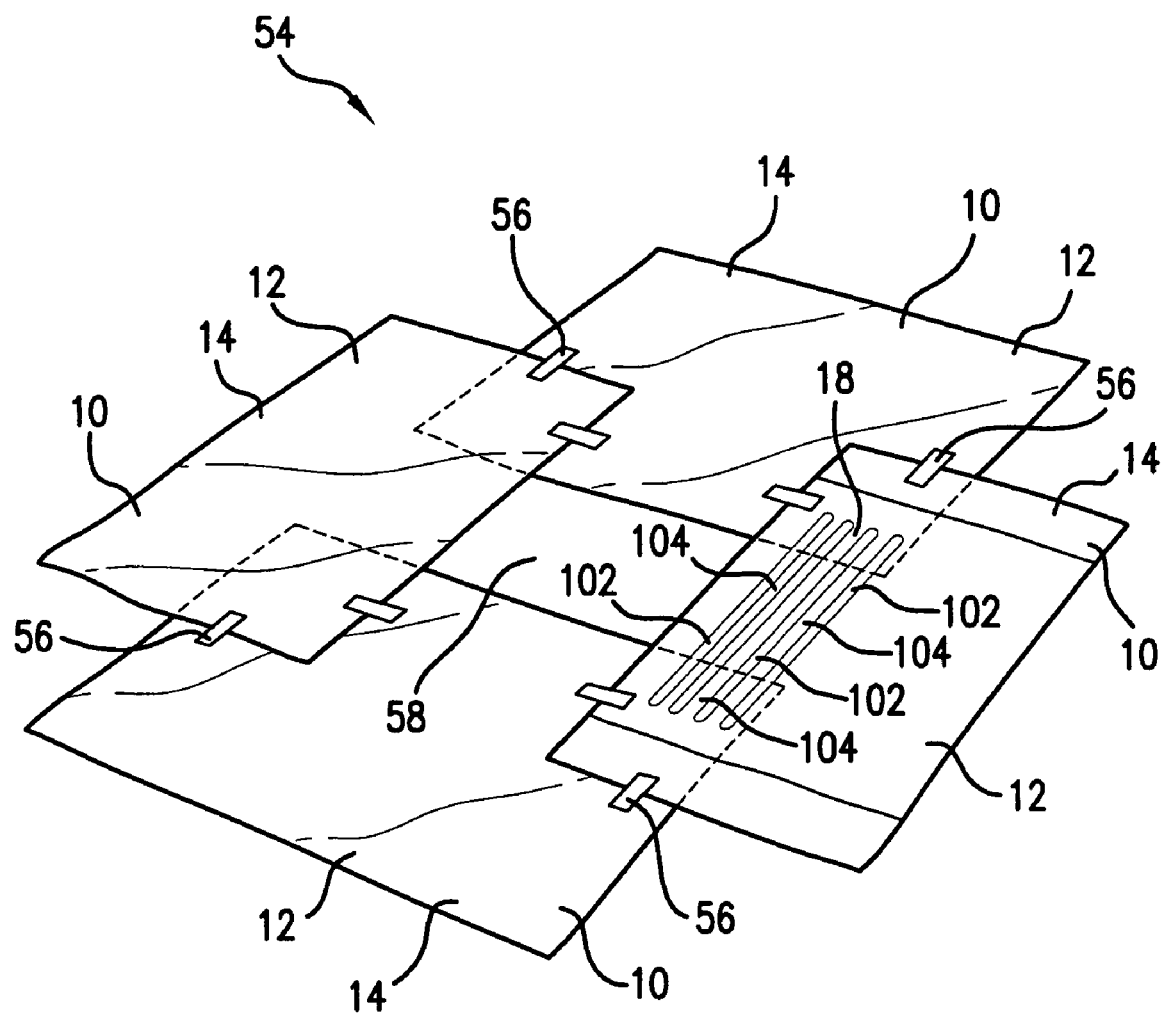
FIG. 19 is a perspective view of a plurality of drapes formed according to one exemplary embodiment of the present invention that are connected together via fasteners to provide a surgical opening.

In another embodiment, such as shown in FIG. 19, a drape kit 54 is provided that includes a plurality of surgical drapes 10 each formed from the fabric 12 and having a base sheet 14. For example, in one embodiment, the drape kit 54 includes at least one hook fastener 56 for securing at least two drapes 10 together. Alternatively, the fasteners 56 may be adhesive strips in other exemplary embodiments of the present invention. As specifically shown in FIG. 19, four drapes 10 and eight hook fasteners 56 are provided. Specifically, each drape 10 is secured to two other drapes 10 via two hook fasteners 56. However, it should be understood that the drapes 10 can be attached to each other using other methods as well.

The drape kit 54 may include any number of drapes 10 greater than one. As shown, the four drapes 10 are arranged so as to define a surgical opening 58 between the drapes 10. Such an opening 58 could be created by medical personnel for performing a surgical technique on a patient without the need for a specifically designed drape 10. Thus, the drapes 10 of the drape kit 54 could be arranged in any desired manner over the top of a patient and operating table to provide much greater flexibility to the medical personnel. Also, the number of different specific drapes 10 that might need to be purchased and inventoried is reduced through use of the drape kit 54.

Various embodiments of the materials and methods used to construct a surgical drape in accordance with the present invention will now be described in more detail. The fabric 12 may be made from the same or different materials as the base sheet 14. For example, as shown in FIG. 10, the fabric 12, as discussed in more detail below, may be constructed from nonwoven layers, adhesive layers, film layers, etc. Moreover, some or all of the fabric 12 may be constructed so as to be hydrophilic or hydrophobic, and may be chemically treated to achieve the desired water absorbency properties. For instance, the fabric 12 and/or one or more layers of the fabric 12 may be treated with a surfactant in a manner such as described in U.S. Pat. No. 5,540,979, which is incorporated herein in its entirety by reference thereto for all purposes.

As stated, the fabric 12 may be multilayered and may include a non-woven layer disposed on one surface of the fabric 12. The nonwoven layer can generally have a variety of basis weights. For example, in one embodiment, the layer has a basis weight of about 34 grams per square meter. In addition, the nonwoven layer can be formed in a variety of ways and can be formed from a variety of different materials.

Although not required, in addition to the nonwoven layer, additional layers of the fabric 12 may also be provided. For example, two more layers may be secured to the nonwoven layer. In some instances, these additional layers can impart fluid barrier attributes to the drape 10 and improve moisture vapor permeability. For instance, these additional layers can be made from meltblown webs, film materials, and the like.

In one embodiment, a layer of the fabric 12 is a barrier film made from 0.6 mil of polyolefin film. For instance a specific example as produced by Pliant Corporation is known as XP-928 Blue film.

In one embodiment, layers of the fabric 12 are joined to one another by adhesive layers. For example, the adhesive layer can be a meltblown web made from an amorphous polyolefin, such as Rextac 2730, which is sold by Huntsman Corporation and has a basis weight of about 3 grams per square meter.

The fabric 12 may in another exemplary embodiment of the present invention be a spunbond layer attached to a middle layer of a meltblown material which is further attached to a backing layer being a fluid impervious film. This type of an arrangement for the fabric 12 allows for the reinforcement of the area surrounding the fenestration 16 and also allows for fluid absorption. Construction of such a fabric 12 is described in U.S. Pat. No. 4,379,192 to Wahlquist et al. which is incorporated by reference herein in its entirety for all purposes. The absorbent properties present in the spunbond layer and to some extend the film may be polymers and treatments that are described in U.S. Pat. No. 5,540,979 to Yahiaoui et al. which is incorporated by reference herein in its entirety for all purposes.

A diverting feature 18 is located within the drape 10 and is capable of being made by an embossing process. In forming the diverting feature 18 of the present invention, in one exemplary embodiment an embossing plate 22 as shown in FIG. 1 is provided. The embossing plate 22 has a plurality of flat channels 60, 62, 64, 66, and 68 cut on one surface that are separated by uncut continuous regions.

Figure 22:
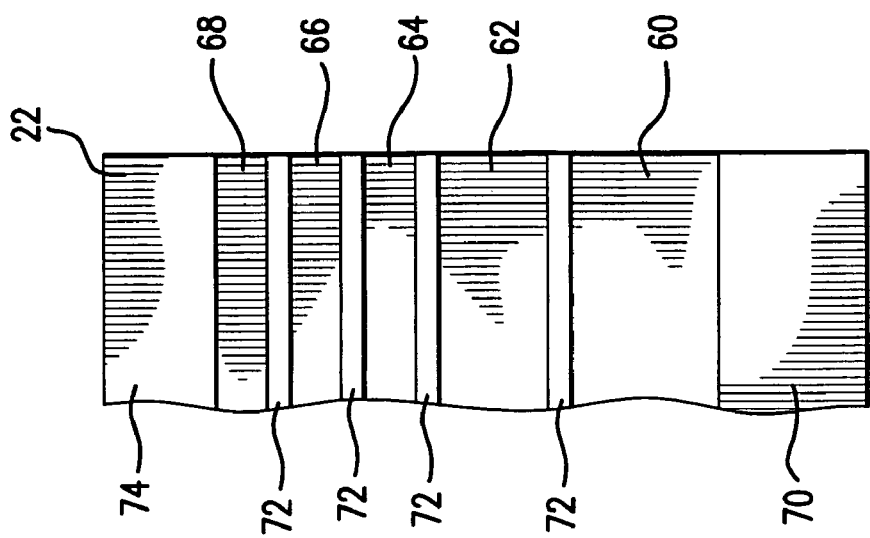
FIG. 22 is a detailed top plan view of one section of the embossing plate shown in FIG. 20.
Figure 21:
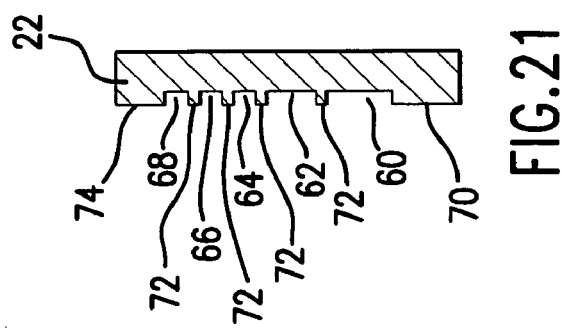
FIG. 21 is a cross sectional view taken along line 21 of the embossing plate shown in FIG. 20.
Figure 20:
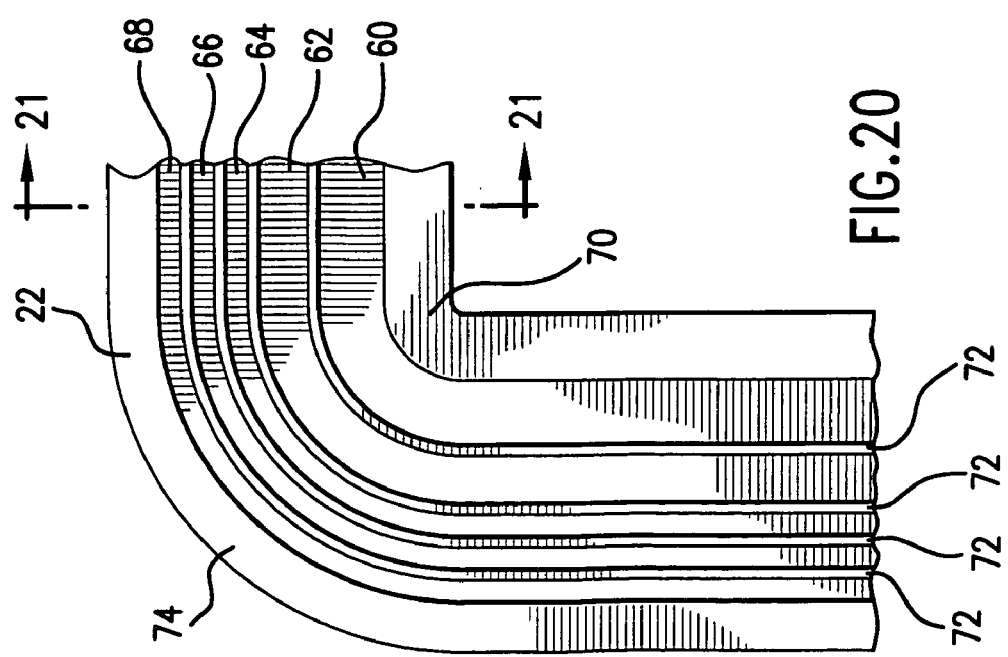
FIG. 20 is a partial top plan view of an embossing plate that is used to form the diverting feature in accordance with one exemplary embodiment of the present invention.

The embossing plate 22 may be seen in greater detail in FIG. 20. Here, a portion of the embossing plate 22 that is used in order to form the diverting feature 18 is shown. A cross-sectional view of the embossing plate 22 is shown in FIG. 21, and a detailed close up view of the embossing plate 22 is shown in FIG. 22. The channels may include a channel 60 that is 20 mm wide, a channel 62 that is 15 mm wide, and a series of channels 64, 66, and 68 that are each 7 mm wide. An uncut region 70 that is 20 mm wide is present next to the channel 60. Also, a series of uncut regions 72 that are 3 mm wide are positioned between the channels 60, 62, 64, 66, and 68. Additionally, an uncut region 74 that is 15 mm wide is located next to the channel 68. The channels 60, 62, 64, 66, and 68 may be of the same depth or may be of various depths. These depths could include, for instance, 3 mm or 1 mm. Additionally, in other exemplary embodiments of the present invention, any number of the channels may be used, those channels having either the same or varying widths and/or depths.

The embossing plate 22 may be used in order to produce the diverting feature 18 of the fabric 12 without excessive densification of the fiber structure or fusing into the film backing if present. As can be seen in FIG. 1, the fabric 12 may be positioned between the embossing plate 22 and a section of a resilient member 24 such as a resilient foam. A flat base plate 26 is provided onto which the foam 24 rests. A fixed plate 20 is located adjacent to and contacts the embossing plate 22. By applying force in the direction of the arrow (F) shown in FIG. 1 and upon using an appropriate amount of time and temperature, the diverting feature 18 may be imparted onto the fabric 12 with the arrangement shown in FIG. 1.

The foam 24 may be a high temperature resistant rubber that is deformable and completely recovers its original thickness after compression. In one exemplary embodiment of the present invention, the temperature of the embossing plate 22 may be in the range of from 53.33° C. to 66.94° C. having a set point temperature of 62.78° C. The time duration needed in order to impart the diverting feature 18 onto the sheet 14 may be two minutes of actual compressive force. Further, the pressure applied by the force (F) may translate to 137895 Pascals on the base plate 26.

The embossing method employed by the present invention seeks to prevent the fiber and film components of the fabric 12 from fusing either partially or completely as opposed to simply being densified. The present invention may therefore seek to densify the fabric 12 such that some degree of the fiber structure is maintained on the non-woven component of the fabric 12. When partial to complete fusing of the fabric 12 occurs, the absorbent attributes of the fabric 12 are substantially sacrificed since fluid will remain on the surface of the fabric 12.

The fabric 12 may be positioned between the foam 24 and the embossing plate 22 such that either the spunbond layer or the film, as discussed in the exemplary embodiment of the fabric 12 above, faces either the embossing plate 22 or the foam 24. As such, the present invention is not limited to an up or down orientation of the fabric 12 between the embossing plate 22 and the foam 24.

This method produces a series of raised areas between the channels in the fabric 12. Although shown as having only one embossing plate 22, in other exemplary embodiments of the present invention a second embossing plate 22 may be used where the first and second embossing plates 22 have matching male and female grooved portions. These grooves may also be used to produce the channels in the fabric 12.

Regardless of the actual construction of the surgical drape 10, the surgical drape 10 is provided with the diverting feature 18. The purpose of the diverting feature 18 is to preferentially direct fluid that is spilled onto the drape 10. The diverting feature 18 as shown in the exemplary embodiment in FIG. 10 may consist of a series of raised areas 104 on the fabric 12 and a series of channels 102 on the fabric 12. The channels 102 may be spaced between the raised areas 104. However, it is to be understood that in other exemplary embodiments of the present invention that the channels 102 may be separate from the raised areas 104.

Figure 11:
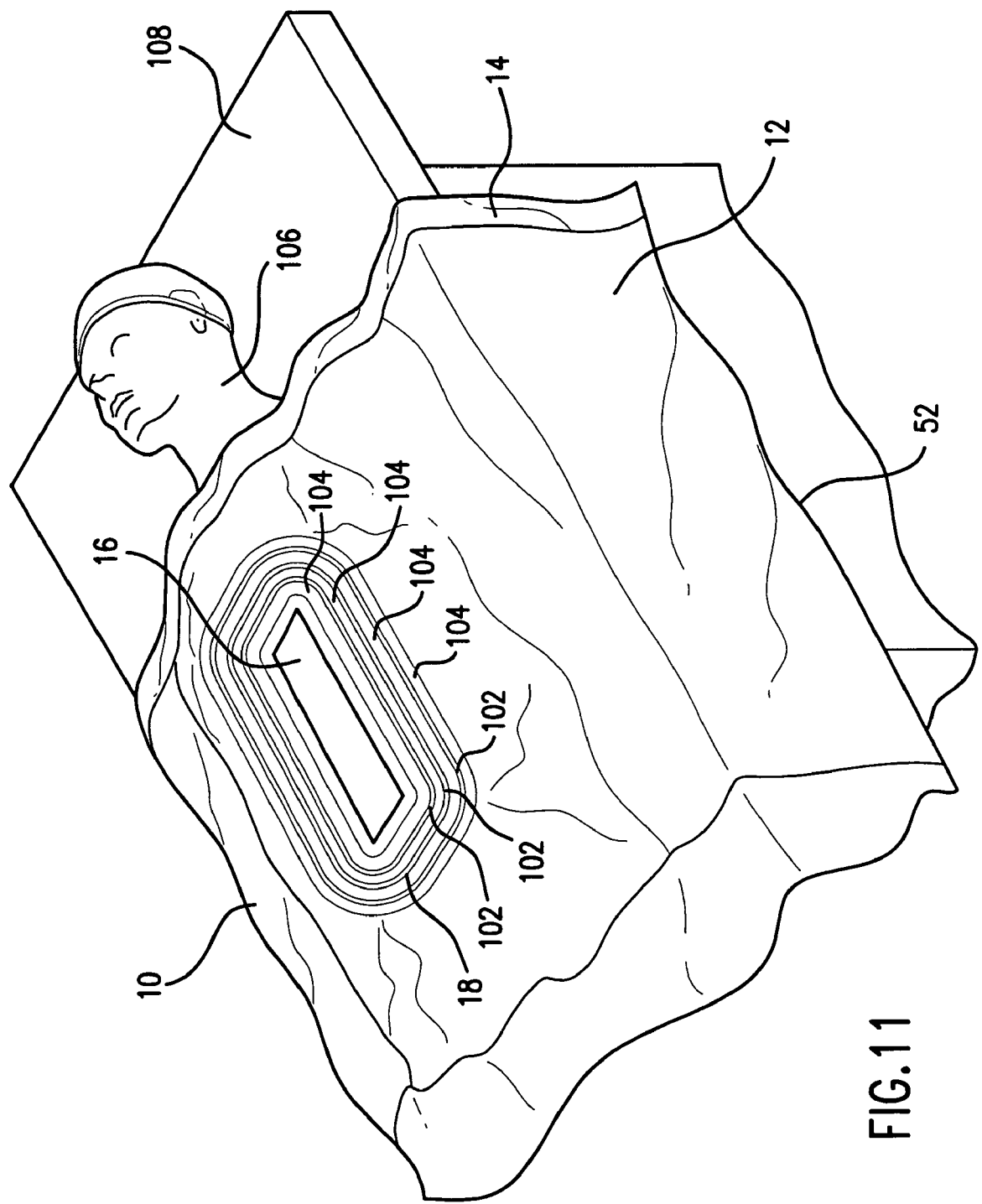
FIG. 11 is a perspective view of an exemplary embodiment of a drape in accordance with the present invention. The drape is shown as being placed on a patient.

The diverting feature 18 contributes to the management of fluids that are spilled onto the drape 10 by directing the fluid in and along the channels 102. Additionally, the fluid may be directed in and along the raised areas 104. FIG. 11 shows the surgical drape 10 being placed on a patient 106 situated on an operating table 108. In this instance, the fenestration is located on the chest of the patient 106. Fluids spilled close to the fenestration 16 would travel, due to gravity, away from the fenestration 16 since it is located in a substantially high point of the drape 10. The presence of the diverting feature 18 tends to retard the natural flow of the fluid caused by gravity. The channels 102 are in this instance densified sections of the fabric 12 that are depressions of the surface of the fabric 12. The channels 102 may be aligned so as to be perpendicular to the natural flow path of the fluid caused by gravity. In this instance, once the fluid contacts the channels 102 the channels 102 act to wick and spread the fluid in the direction of the channels 102. As the fluid is spread, it is absorbed by the channels 102 and other portions of the fabric 12 due to the fact that the channels 102 retain some degree of the absorbency present in the fabric 12.

Figure 12:
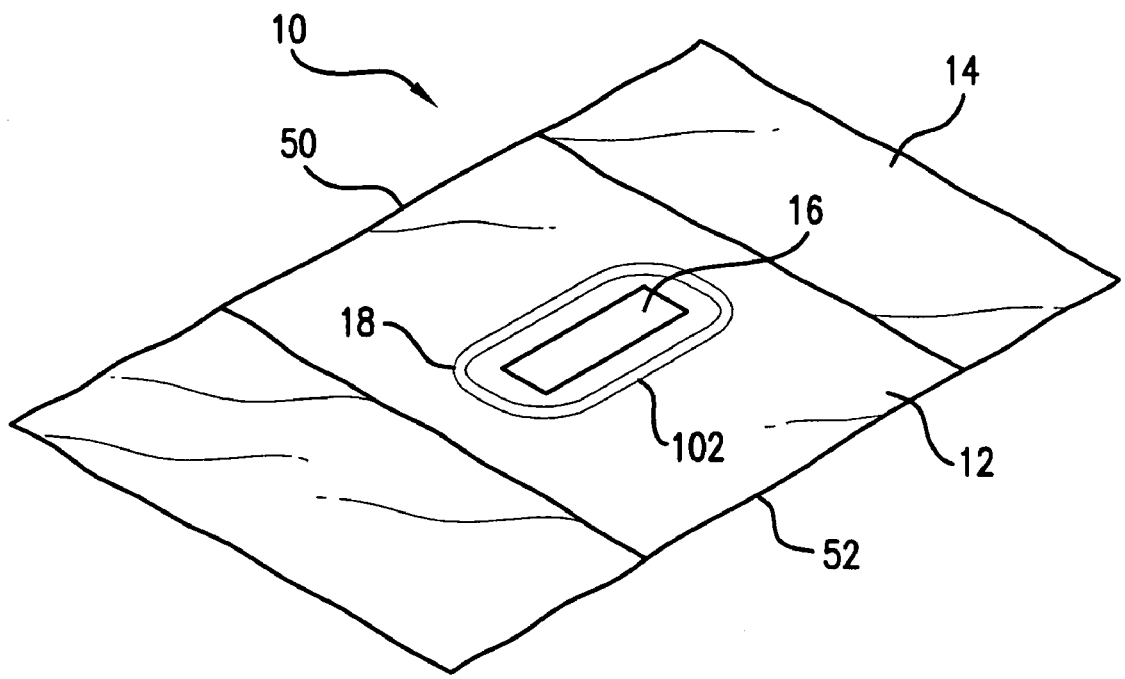
FIG. 12 is a perspective view of an alternative exemplary embodiment of the drape in accordance with the present invention. The diverting feature includes a channel section that completely surrounds the fenestration.

Although as described as being channels 102, the diverting feature 18 may consist of only the raised area 104. Alternatively, the diverting feature 18 may include any combination of the channels 102 and/or the raised areas 104. The diverting feature 18 of the present invention is not limited to having a channel 102 being a certain depth or length. Additionally, the diverting feature 18 may include the raised areas 104 being of any shape, length, or height. FIG. 12 shows another exemplary embodiment of the drape 10 in accordance with the present invention. Here, the diverting feature 18 consists of only a single channel 102 proximate to the fenestration 16. The channel 102 is located on the fabric 12 and may be of any depth. The channel 102 completely surrounds the fenestration 16 so that when fluids spilled proximate to the fenestration 16 flows across the surface of the fabric 12, it will contact the channel 102 and be spread along the channel 102.

Figure 13:
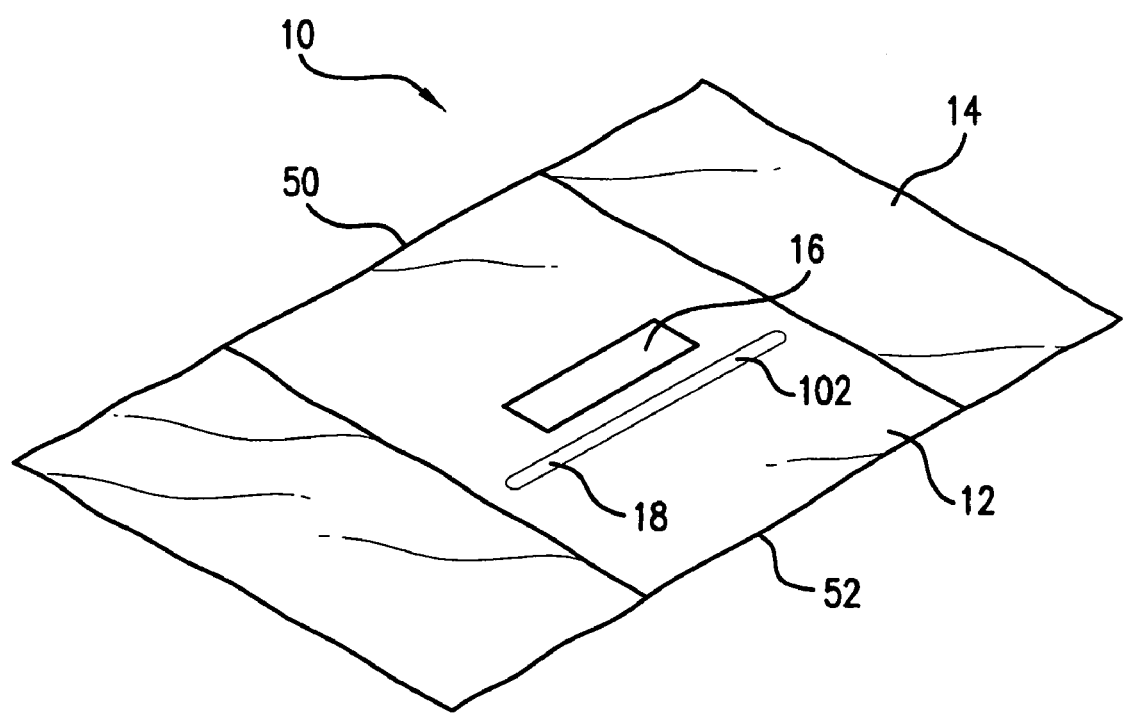
FIG. 13 is a perspective view of an alternative exemplary embodiment of a drape in accordance with the present invention. Here, the diverting feature comprises a single channel that is located proximate to the fenestration.

FIG. 13 shows another exemplary embodiment of the present invention where the drape 10 is provided with a single channel 102. The channel 102 is provided proximate to the fenestration 16 and includes a single, substantially straight section. The drape 10 may be situated such that the fenestration 16 is above the diverting feature 18 so that when fluid spilled proximate to the fenestration 16 flows downward, it contacts the channel 102 and is spread along the channel 102.

Although described as being located on the fabric 12, it is to be understood that in other exemplary embodiments of the present invention that the diverting feature 18 may be incorporated into the drape 10 where the drape 10 does not have the fabric 12 being present, but only includes the sheet 14. Such an arrangement is shown in FIG. 14. Here, the diverting feature 18 is located around the fenestration 16 and comprises three channels 102 that are separated from one another by two raised areas 104. Two other raised areas 104 also separate the channels 102 from portions of the sheet 14 that do not include the diverting feature 18. Although shown as completely surrounding the fenestration 16, it is to be understood that the diverting feature 18 may surround only a portion of the fenestration 16 in other exemplary embodiments.

Figure 15:
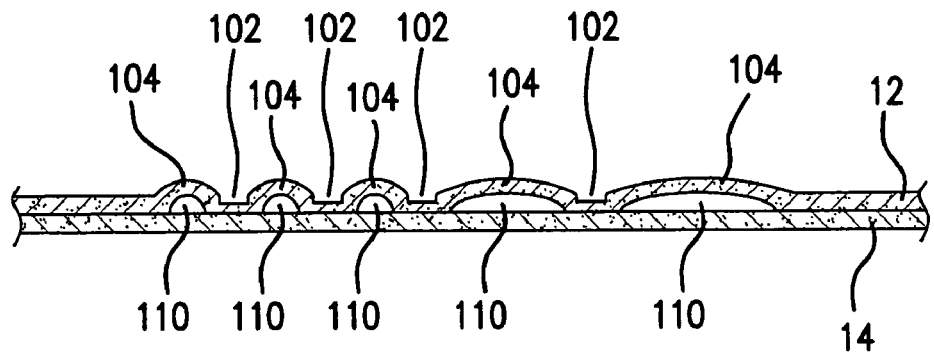
FIG. 15 is a cross sectional view of an exemplary embodiment of a diverting feature in accordance with the present invention. Here, channels forming the diverting feature are of substantially the same size and shape, while some of the raised areas that form the diverting feature are of different sizes and shape.
Figure 16:
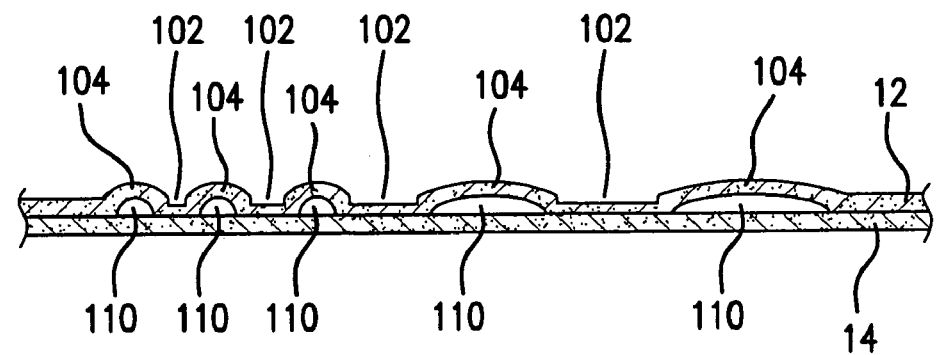
FIG. 16 is a cross sectional view of an alternative exemplary embodiment of the diverting feature in accordance with the present invention. Here, some of the channels and the raised areas that form the diverting feature of are of different sizes and shapes.

FIG. 15 shows a cross-sectional view of another exemplary embodiment of the sheet 14 used in accordance with the present invention. Here, the diverting feature 18 is shown as being a series of raised areas 104 immediately adjacent to a series of channels 102. The channels 102 are shown as being depressions in the surface of the fabric 12, and the raised areas 104 are shown as extending above the majority of the surface of the fabric 12. The width of the raised areas 104 are the same in some instances and are different in others. For example, the width of the three raised areas 104 on the left side of the fabric 12 as shown in FIG. 15 have the same width, while the two raised areas on the right side of the fabric 12 have a width that is greater than the previously mentioned three raised areas 104. As such, the present invention is not limited to having the raised areas 104 being of the same width, height, or shape. Additionally, the channels 102 that are used in the present invention may be of different depths, widths, or shapes. In fact, FIG. 16 shows an exemplary embodiment of the present invention where the channels 102 have different widths. In this regard, some of the raised areas 104 may be spaced at different distances from the adjacent raised area 104 due to the fact that the channels 102 may be of varying widths.

Voids 110 may be present between the fabric 12 and the sheet 14. These voids 110 may be filled in with a material in other exemplary embodiments of the present invention. Further, the sheet 14 and the fabric 12 may be formed such that the voids 110 are not present in other exemplary embodiments of the present invention.

Figure 15A:
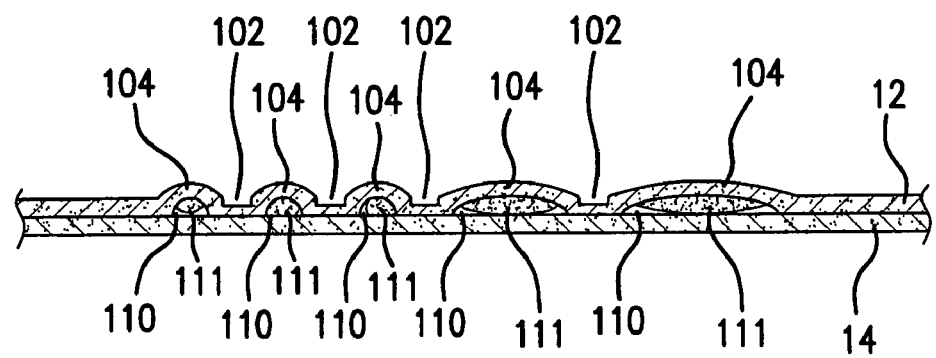
FIG. 15A is a cross sectional view of an exemplary embodiment of a diverting feature in accordance with the present invention. Here, material is located between the sheet and the fabric.

FIG. 15A shows an exemplary embodiment of the present invention where material 111 is located between the fabric 12 and the sheet 14 inside of the voids 110 present in FIG. 15. The material 111 may fill completely or partially the voids 110. The material 111 may be any type of material, for instance it may be a material that ensures that the channels 102 and the raised areas 104 retain their respective shapes despite the application of compressive forces. Compressive forces could be imparted onto the drape 10 for instance during packaging and by being used in certain applications. Examples of materials 111 that may be used include resilient materials such as foams which may be opened or closed cell. Also, non-woven fabrics that contain meltblown, spunbond, and/or carded staple fibers may be used as the material 111. These materials 111 help to retain the channels 102 and the raised areas 104 without substantially increasing the weight of the diverting feature 188.

Although the exemplary embodiments shown in FIGS. 15 and 16 show alternating raised areas 104 and channels 102, it is to be understood that the present invention also encompasses exemplary embodiments where two raised areas 104 are located next to one another without one of the channels 102 being present. Additionally, the present invention also encompasses exemplary embodiments where multiple channels 102 are located next to one another without one of the raised areas 104 located therebetween. As such, the present invention includes any combination of the raised areas 104 and/or the channels 102.

Figure 17:
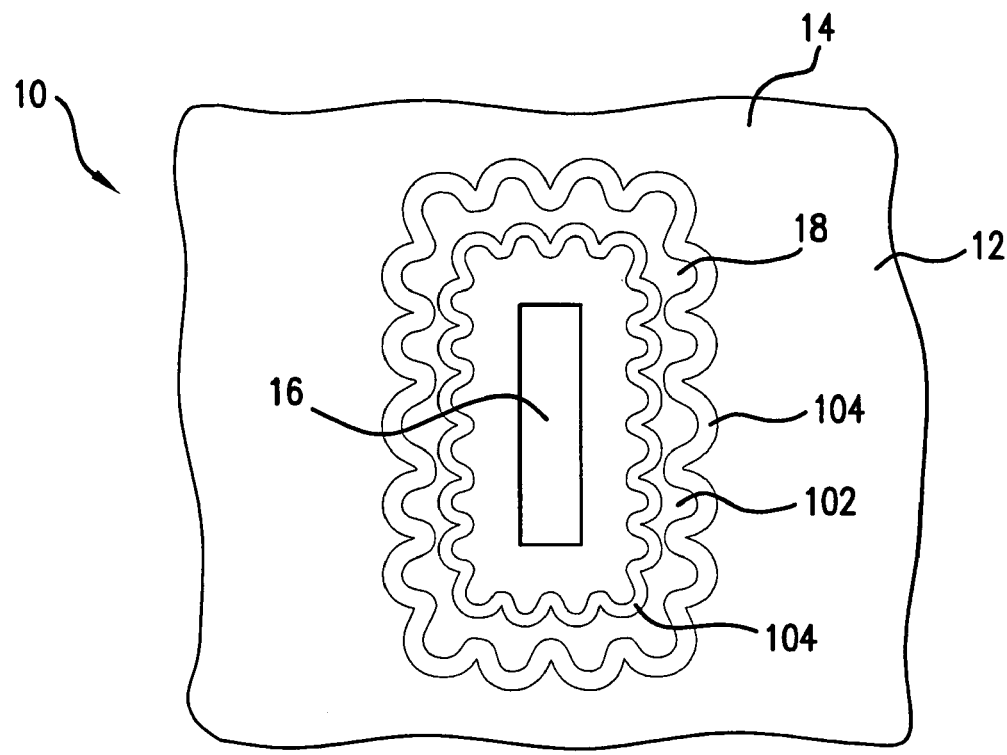
FIG. 17 is a top plan view of an alternative exemplary embodiment of a drape in accordance with the present invention. Here the diverting feature is shown as having an alternative shape and size.
Figure 18:
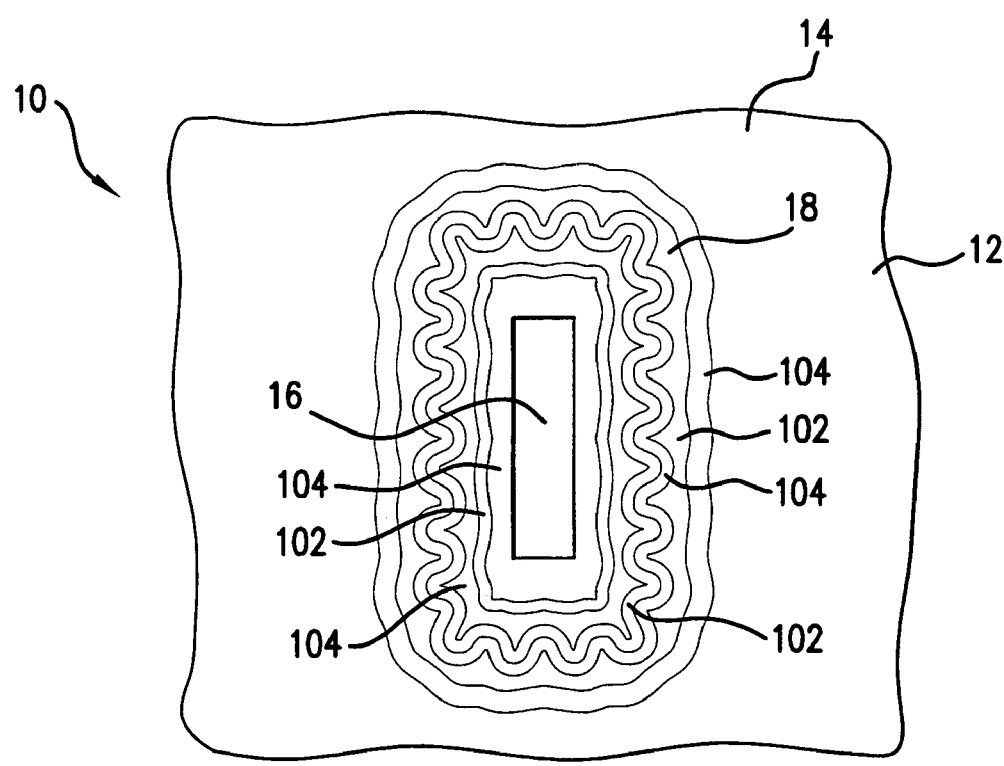
FIG. 18 is a top plan view of an alternative exemplary embodiment of a drape in accordance with the present invention. The diverting feature is shown as having an alternative size and shape.

As stated, the channels 102 and the raised areas 104 may be of varying shapes. FIG. 17 shows such an instance where the diverting feature 18 includes channels 102 and raised areas 104 that are of an unconventional shape. Another exemplary embodiment of the present invention is also shown in FIG. 18 where the raised areas 104 and the channels 102 of the diverting feature 18 are of different shapes and sizes.

The diverting feature 18 may therefore be made of the same material as the fabric 12 and/or the sheet 14. Also, the material of the diverting feature 18 may be of a higher or lower density than the surrounding portions of the material of the fabric 12 and/or the sheet 14. Also, the diverting feature 18 may include the channels 102 and the raised areas 104 that are of fabric having substantially the same fluid absorbent properties of the fabric 12 and/or the sheet 14. For instance, the fabric of the channels 102 and/or the raised areas 104 may be capable of absorbing greater than 90% of the same amount of fluid as other portions of the fabric 12 and/or the sheet 14. Additionally, the fabric of the channels 102 and the raised areas 104 may be capable of absorbing greater than 75% of the same amount of fluid as other portions of the sheet 14 and/or the fabric 12. Also, the fabric of the channels 102 and the raised areas 104 may be able to absorb at least 50% of the fluid that is able to be absorbed by other portions of the fabric 12 and/or the sheet 14. In yet other exemplary embodiments of the present invention, the fabric of the diverting feature 18 is capable of absorbing 100% of the same amount of fluid that the sheet 14 and/or the fabric 12 are capable of absorbing. Finally, the present invention includes exemplary embodiments where the fabric of the channel 102 and the raised area 104 are capable of absorbing fluid at any amount greater than 0% of the same amount of fluid that is able to be absorbed by the fabric 12 and/or the sheet 14.

It should be understood that the present invention includes various modifications that can be made to the embodiments of the surgical drape 10 as described herein as come within the scope of the appended claims and their equivalents.

Experiment Carried out in Accordance with one Exemplary Embodiment of the Present Invention The densification of the fabric 12 due to the diverting feature 18 may be described by comparing the thickness of the fabric 12 in unembossed regions to embossed regions. These thickness measurements may be made by using a dial micrometer of the type specified in ASTM standard D 3577-99 which is also used for measuring the palm thicknesses of fluid impervious gloves. In particular, the dial micrometer used had a 0.6 mm diameter foot and a 50 gram weight for consistent compressive force during the measurement.

FIG. 2 shows thickness values that are reported as the average values of at least three repetitions on an individual sample of fabric 12. Region A is embossed fabric 12 that corresponds to a 20 mm wide channel in the embossing plate 22. Region B corresponds to a 15 mm wide channel and Region C corresponds to a 10 mm wide channel.

FIG. 3 shows thickness values for samples of the fabric 12 that are embossed at identical conditions except for the position of the fabric 12 and the thickness of the resilient foam 24. The position of the fabric 12 may be thought of as having two possible positions, one where the spunbond layer faces the embossing plate 22 during embossing and the other where the film layer faces the embossing plate 22 during embossing. The embossing method used on the samples in FIG. 3 have a time duration of 2 minutes and a set point temperature of the fixed plate 20 being 63.89° C. The thickness values represent an averaging of at least 4 measurements for 5 plies of individual samples stacked on top each other divided by 5 (the number of plies). The table also shows the result of the respective differences between the values for the unembossed regions and the embossed regions divided by the unembossed region value. This number is multiplied by 100 to obtain the percentage change in thickness from embossing as shown. In the samples identified in FIG. 3, the maximum distance of the raised regions from the bottom of the channels was between 0.15 and 0.2 cm.

In order to determine the effect that embossing had on the absorbency of the embossed regions versus the unembossed fabric, an absorbency test was conducted. The absorbency test was performed according to Federal Government Specification UU-T-595b. A test sample being 10.16 cm by 10.16 cm is weighed and is then saturated with water for 3 minutes by soaking. The sample is then removed from the water and hung by one corner for 30 seconds to allow excess water to be drained off. The sample is then reweighed, and the difference between the weight and the dry weight is the water pick up of the sample expressed in grams per 10.16 cm by 10.16 cm sample. The percent absorbency is obtained by dividing the total water pick up by the dry weight of the sample and then multiplying by 100. The measurements are shown in FIG. 4. The results show a reduction, yet retention of, absorbency in the fabric 12 per 5 repetitions. Despite the densification of the fabric 12 in the embossed regions and the corresponding reduction in absolute maximum absorption capacity as determined by the percentage of absorbency, the incorporation of the embossed channels and raised areas in the fabric 12 provides a fluid control feature by impeding fluid flow due to gravity. The presence of the channels separated by raised regions acts to slow the gravity induced flow of fluid, which allows more time for the fluid to be absorbed by the fabric 12.

In order to demonstrate this improvement, samples of fabric 12 with embossed regions as diverting features at different locations made in the fabric 12 were prepared. The direction of the embossed channels were positioned perpendicular to the direction of the intended gravity induced fluid flow. The samples were tested using an apparatus and test method similar to the one described in the run off test section of U.S. Pat. No. 5,258,221 to Meirowitz et al. which is incorporated by reference herein in its entirety for all purposes. However, the test is modified from the run off test as described in Meirowitz.

Figure 5:
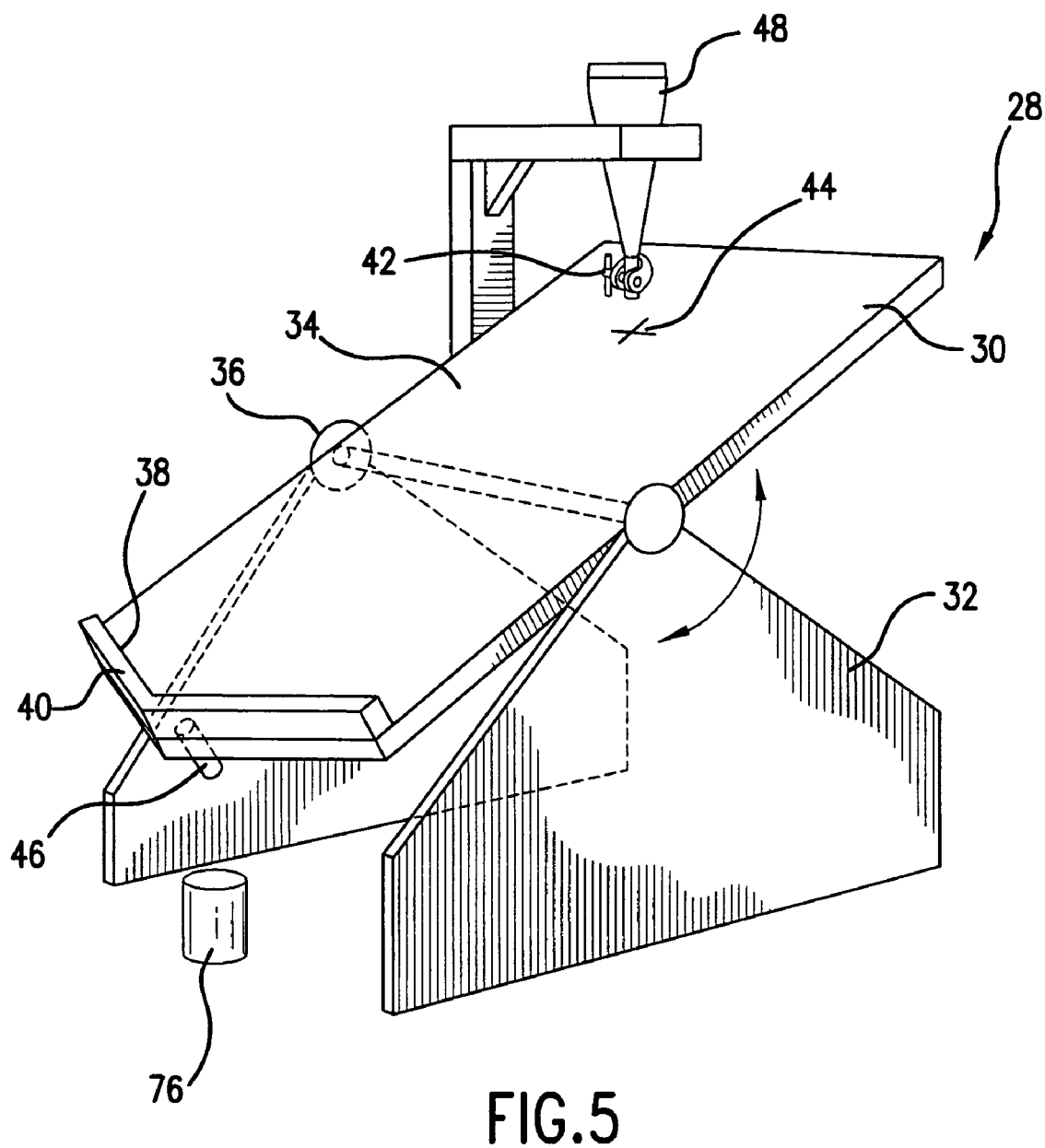
FIG. 5 is a perspective view of a run-off apparatus that is used to measure the absorbency and the flow pattern imparted on drapes in accordance with the present invention.

The modified run off test therefore uses a run off apparatus 28 as shown in FIG. 5. Here an adjustable inclined platform 30 is provided that is supported on a horizontal surface. The inclined platform 30 has a base 32 and an inclined surface 34. The inclined surface 34 has a width of 25.4 cm and a maximum length along its transverse centerline of 55.88 cm. The inclined surface 34 is inclined at preset angles by pivoting the inclined surface 34 about a support member 36 that is attached to the inclined surface 34 at a position equidistant from its maximum length. Located at a bottom edge 38 of the inclined surface 34 is a V-shaped barrier 40. The V-shaped barrier 40 serves to funnel liquid running down the inclined surface 34 into a hole 46 located in the center of the V-shaped barrier 40.

Suspended above the inclined surface 34 is a dispensing funnel 48. The dispensing funnel 48 is adapted to hold at least 15 mm of a liquid. The liquid can be released through a valve 42 onto the inclined surface 34 onto a targeted location 44. The height of the valve 42 above the inclined surface 34 is adjustable in order to allow for a clearance of 10 mm between the valve 42 and a sample to be tested when in position on the inclined surface 34. A generally rectangular test sample 25.4 cm wide and 35.56 cm long may be provided. The test sample may be mounted on the inclined surface 34 so that the bottom of the sample touches the top of the V-shaped barrier 40. The top of the sample extends beyond the dispensing funnel 48 and the targeted location 44. The test sample may be held in place by a weight on the top of the fabric 12. The test sample may be generally centered on the inclined surface 34 and the dispensing funnel 48 may be centered from each side edge of the incline platform 30 and 23.5 cm from the top of the V-shaped barrier 40 so that the fluid impacts the sample at the targeted location 44 independent of the position of the inclined surface 34 with respect to the horizontal support surface. A collection device 76 may be placed under the hole 46 in order to collect fluid draining there through. After positioning the test sample, the valve 42 is opened to dispense the fluid contained in the dispensing funnel 48 within 15 seconds. The amount of fluid which runs off of the test sample and is collected in the collection device 76 through the hole 46 is recorded as the run off in grams. The difference between the run off and the weight of the dispensed fluid is the amount absorbed by the test sample.

Fabric 12 with and without embossed channels was evaluated by the modified run off test using a standard set of conditions. 15 mm of red tinted saline was placed in the dispensing funnel 48 for testing with each fabric 12 sample. The saline had an ambient temperature of 21.1° C. and weighed 15 grams. The angle of the inclined surface 34 used was at 15°, 25°, 30°, and 45°. The samples of the fabric 12 were cut to 25.4 cm wide by 35.56 cm long and each were weighed before testing.

Samples of the fabric 12 were prepared for testing by the modified run off test having the embossed regions and unembossed regions as previously described. For samples having embossing, the location, type, and number of embossing channels are listed in FIG. 6. Descriptions of the sample series will be later described. In order to account for differences among the absorbent attributes due to fabrication variations of the fabric 12 used to prepare each sample, for example basis weight, variability of the spunbond and/or meltblown components, treatment variability, starting thicknesses, etc., the run off value collected for each test was "normalized" by dividing the weight of each respective sample and recorded as normalized run off. The values reported in the table represent an averaging of at least 4 individual measurements from the modified run off test, weight determinations, and the related normalized run off calculations. Lower normalized run off values represent samples with less fluid run off. A representative example of such averaging is included with the description of sample series 8 used at an inclined surface 34 of 25°.

From the average values shown in FIG. 6, at low angles of the inclined surface 34, the samples with embossed channels impede fluid run off so that more fluid can be absorbed compared to fabric 12 without embossed channels. As the angle of incline of the inclined surface 34 is increased, the fluid impedance effect with the amount of test fluid is not as discernable via the modified run off test.

Sample series 8 represents fabric 12 samples that were prepared using the embossing plate 22 shown in FIG. 1 for straight portions of embossed channels with the spunbond component facing the embossing plate 22 during embossing. The edge of the embossing plate 22 nearest the 20 mm cut channel was positioned at the bottom edge of the fabric 12. This imparted five raised regions separating channels in the fabric 12 to impede gravity induced fluid flow. This is described as being "Edge embossed 5 ridges" in FIG. 6. For this series, twelve fabric 12 samples were prepared in this manner, weighed, and tested via the modified run off test. The individual measurements and the resulting average used in FIG. 6 for the sample 8 series tested at an incline angle of 25° are shown in FIG. 7.

Sample series 9 represents a set of twelve additional fabrics prepared in the same way as sample series 8, but at a different day in order to verify the validity of the preparation, measurements and results.

Sample series 10 represents a set of four fabrics 12 embossed in the manner of those for sample series 8 except that the position of the embossing plate 22 was reversed 180° and the edge of the embossing plate 22 nearest the 20 mm cut channel was placed approximately 6.35 cm from the bottom edge of the fabric in order to impart two raised regions. The two raised regions may be two ridges that are approximately 20 mm and 15 mm and separate two channels, each being approximately 3 mm. This accounts for the description in FIG. 6 as being "Partial Embossed 2 ridges".

Sample series 11 represents a set of four fabrics 12 that are embossed in the manner of those for sample series 10 except that the position of the embossing plate 22 was reversed 180° and the edge of the embossing plate 22 nearest the outer most 7 mm cut channel was placed approximately 6.35 cm inches from the bottom edge of the fabric 12. This was done in order to impart 3 raised regions, that being 3 ridges approximately 7 mm each. The 3 raised regions are separated by 2 channels being approximately 3 mm each. The description in FIG. 6 of sample series 11 is therefore "Partial Embossed 3 ridges".

Sample series 12 represents a set of 8 fabrics 12 embossed in the same manner of those for sample series 8 with the exception that the position of the embossing plate 22 was turned over so that the flat face of the embossing plate 22 faced the spunbond component of the fabric 12.

Sample series 13 is a set of twelve fabrics 12 embossed in the same manner of those for sample series 9 except that the position of the embossing plate 22 during embossing was shifted 10.16 cm away from the bottom edge of the fabric 12.

Sample series 14 represents a set of four fabrics 12 embossed in the manner of those for sample series 9. However, the fabric 12 was embossed with the film component facing the embossing plate 22.

Sample series 15 is a set of eight fabrics 12 embossed in the same manner of those for sample series 9 except that the position of the embossing plate 22 was reversed 180° and the edge of the embossing plate 22 nearest the outer most 7 mm cut channel was placed at the bottom edge of the fabric 12.

Sample series 16 represents a set of twelve fabrics 12 without any embossing, but of the same fabric 12 used for all of the embossed samples. Sample series 16 is a control sample.

Figure 8:
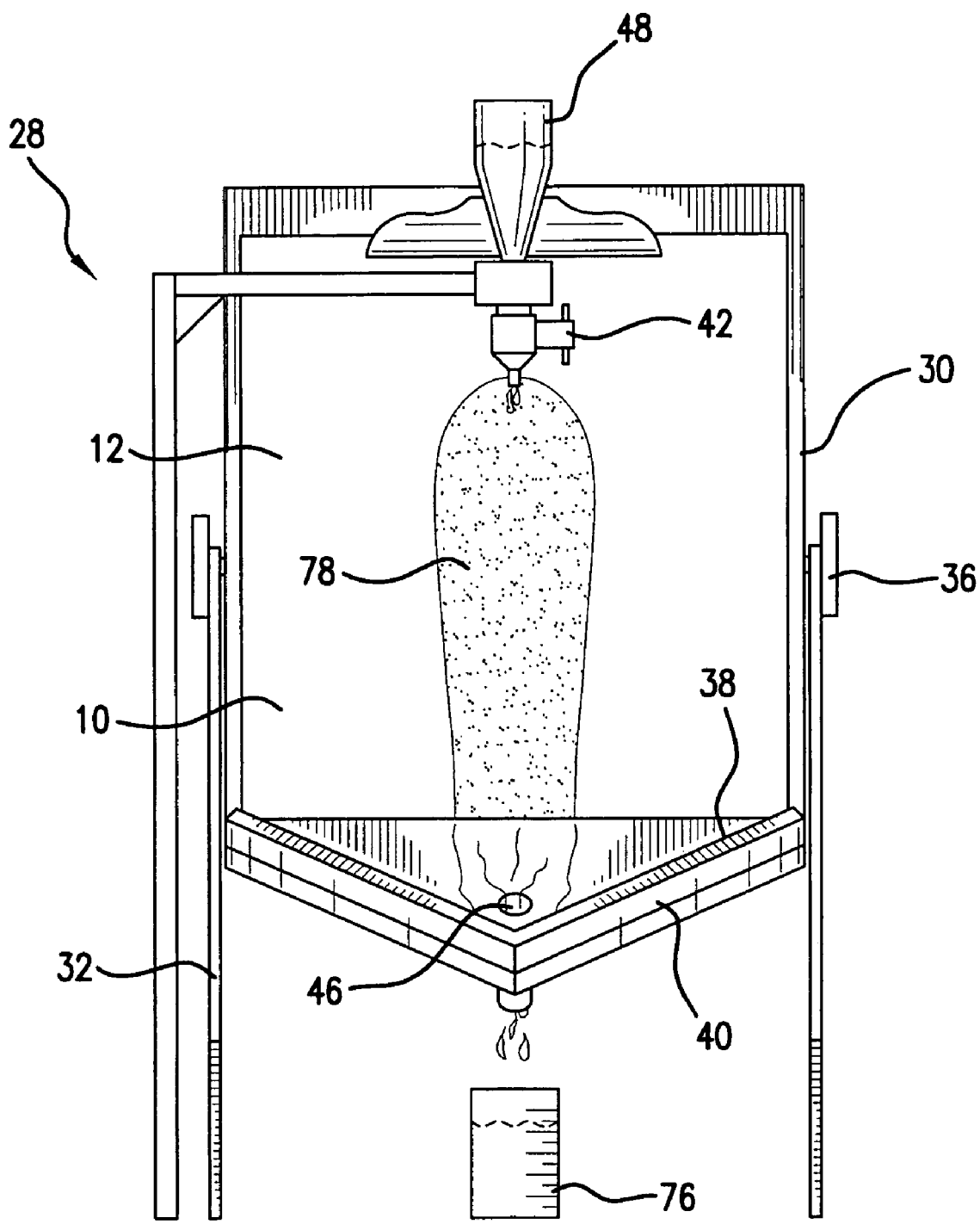
FIG. 8 is a front elevation view of the run off apparatus having the absorbent drape fabric being located thereon. A fluid flow path of fluid dispensed onto the drape is shown.

FIG. 8 shows the run-off apparatus 28 being set such that the inclined platform 30 is set at a 25° angle. The valve 42 is opened and fluid is dispensed onto the surface of the fabric 12 that is located on the inclined platform 30. The fluid flows down across the surface of the fabric 12 in the shape of a fluid flow path 78 as shown. As can be seen, the fluid leaves the surface of the inclined platform 30 through the hole 46 and is collected in the collection device 76. The fluid flow path 78 is a substantially linear path. The fluid flow path 78 is spread out across the fabric 12 due in part to some degree of absorption of the fluid.

Figure 9:
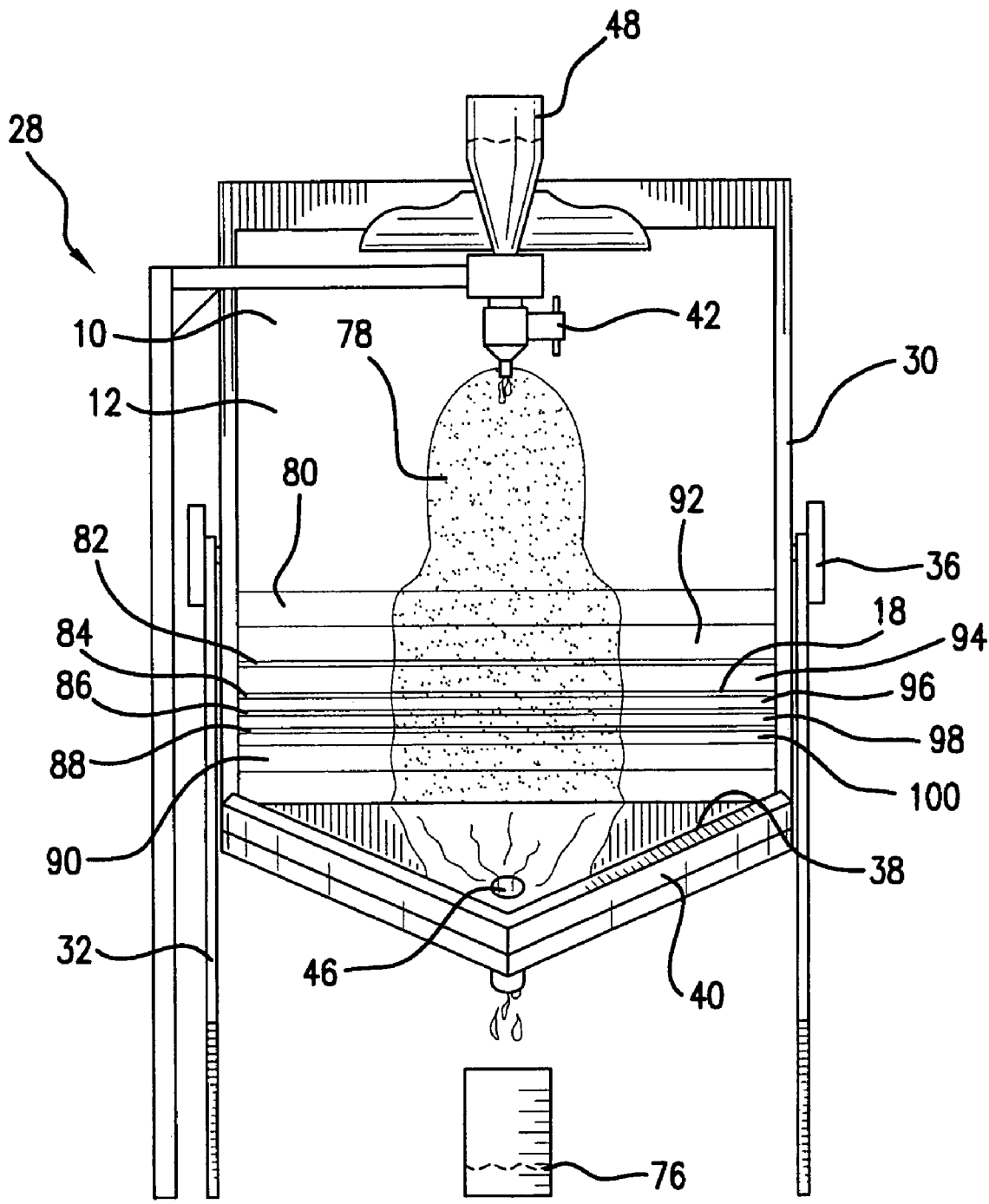
FIG. 9 is a front elevation view of the run off apparatus having an absorbent drape fabric with a diverting feature being located thereon. The fluid flow path of the fluid dispensed onto the drape is shown and may be seen as traveling at least partially along the length of the channels and the raised areas that comprise the diverting feature.

FIG. 9 shows the run-off apparatus 28 of FIG. 8 with the inclined platform 30 again being set at a 25° angle. Here, however, the fabric 12 is provided with the diverting feature 18. The diverting feature 18 includes a plurality of channels 80, 82, 84, 86, 88, and 90. The diverting feature 18 also includes a series of raised areas 92, 94, 96, 98, and 100. The diverting feature 18 is formed by the method as previously discussed with regards to FIGS. 20–22. In this case, the channels 60, 62, 64, 66, and 68 in FIG. 20 form the raised areas 92, 94, 96, 98, and 100 respectively. Additionally, the uncut regions 70, 72, and 74 in the embossing plate 22 of FIGS. 20–22 form the channels 80, 82, 84, 86, 88, and 90 as shown in FIG. 9.

As can be seen in FIG. 9, the fluid flow path 78 is different upon using the fabric 12 provided with the diverting feature 18. Fluid flows across the surface of the fabric 12 and is absorbed in substantially the same manner as the fabric 12 in FIG. 8 until the fluid reaches the channel 80. At this point, the presence of the channel 80 causes the fluid to be spread along the length of the channel 80. Additional contact with the remaining channels and raised areas also urge the fluid to flow in the direction of the channels and raised areas. By spreading the fluid out in this manner, a greater amount of the fluid is absorbed by the fabric 12. The presence of the diverting feature 18 therefore allows for more of the fluid to be absorbed by the drape 10 than would otherwise be the case.

It should be understood that the present invention includes various modifications that can be made to the surgical drape described herein as come within the scope of the appended claims and their equivalents.

What is claimed:

1. A surgical drape for use during surgery on a patient, comprising:
   a sheet configured for covering at least a portion of the patient during surgery, said sheet having an absorbent region; and
   at least one diverting feature located in said absorbent region of said sheet, said diverting feature having at least 50% of the absorbency of said absorbent region of said sheet and said diverting feature having a different density than a section of said absorbent region immediately adjacent to said diverting feature, said diverting feature being integrally formed within said absorbent region, said diverting feature configured for at least partially transferring fluid from one location on said absorbent region to another location on said absorbent region while absorbing at least a portion of the fluid, wherein the position of said diverting feature is stationary with respect to said sheet.

2. The surgical drape of claim 1, wherein said diverting feature is a plurality of channels, said channels being made of the same material as said absorbent region of said sheet, said materials forming said channels being of a higher density than the remainder of said absorbent region.

3. The surgical drape of claim 1, wherein said diverting feature is a plurality of channels embossed on said absorbent region.

4. The surgical drape of claim 1, wherein said sheet has a fenestration included therethrough, and wherein said diverting feature is spread from and surrounds said fenestration.

5. The surgical drape of claim 1, wherein the material of said sheet in said diverting feature is of a higher density than the remainder of said absorbent region, said diverting feature is a plurality of depressed regions in the surface of said absorbent region, said diverting feature being a set of channels connected to one another by depressed rounded segments such that said channels and said depressed rounded segments form a continuous structure.

6. The surgical drape of claim 5, wherein said diverting feature further comprises additional continuous structures each being a set of raised areas connected to one another by raised rounded segments, said additional continuous structures concentric with an adjacent said additional continuous structure on said absorbent region.

7. The surgical drape of claim 1, wherein said diverting feature is a plurality of channels being spaced apart and parallel to one another.

8. The surgical drape of claim 7, wherein all of said channels have the same width.

9. The surgical drape of claim 1, wherein said diverting feature being channels having an elongated portion and a narrow portion, the direction of said elongated portion being perpendicular to the direction of fluid flow on said absorbent region of said sheet.

10. The surgical drape of claim 1, wherein said diverting feature being raised areas having an elongated portion and a narrow portion, the direction of said elongated portion being perpendicular to the direction of fluid flow on said absorbent region of said sheet.

11. The surgical drape of claim 1, wherein said diverting feature is a plurality of channels each being located next to at least one of a plurality of raised sections.

12. The surgical drape of claim 1, wherein said diverting feature being channels having an elongated portion and a narrow portion, the direction of said elongated portion being parallel to at least one edge of said sheet.

13. The surgical drape of claim 1, wherein said diverting feature being raised areas having an elongated portion and a narrow portion, the direction of said elongated portion being parallel to at least one edge of said sheet.

14. A surgical drape for use during surgery on a patient, comprising:
   a sheet configured for covering at least a portion of the patient during surgery, said sheet having an absorbent region;
   at least one diverting feature located in said absorbent region of said sheet, said diverting feature having substantially the same fluid absorbent properties as said absorbent region of said sheet, said diverting feature being integrally formed within said absorbent region, said diverting feature configured for at least partially transferring fluid from one location on said absorbent region to another location on said absorbent region while absorbing at least a portion of the fluid;
   wherein said diverting feature is a plurality of channels each being located next to at least one of a plurality of raised sections; and
   further comprising a resilient material located between a fabric and said sheet, said resilient material being located in a void proximate to said raised section.

15. A surgical drape for use during surgery on a patient, comprising a sheet configured for covering at least a portion of the patient during surgery, at least one diverting feature located on said sheet and having at least 50% of the absorbency of a section of said sheet immediately adjacent to said diverting feature and said diverting feature having a different density than a section of said sheet immediately adjacent to said diverting feature, said diverting feature configured for at least partially transferring fluid from one location on said sheet to another location on said sheet while absorbing at least a portion of the fluid, wherein the position of said diverting feature is stationary with respect to said sheet.

16. The surgical drape of claim 15, wherein said diverting feature is a plurality of channels, said channels being made of the same material as said sheet, the material of said channels being of a higher density than the remainder of said sheet.

17. The surgical drape of claim 15, wherein said diverting feature is a plurality of channels embossed on said sheet.

18. The surgical drape of claim 15, wherein said sheet has a fenestration included therethrough, and wherein said diverting feature is spaced from and surrounds said fenestration.

19. The surgical drape of claim 15, wherein the material of said sheet in said diverting feature is of a higher density than the remainder of said sheet, said diverting feature being a plurality of depressed regions on the surface of said sheet, said diverting feature being a set of channels connected to one another by depressed rounded segments such that said channels and said depressed rounded segments form a continuous structure.

20. The surgical drape of claim 19, wherein said diverting feature further comprises additional continuous structures each being a set of raised areas connected to one another by raised rounded segments, said additional continuous structures concentric with an adjacent said additional continuous structure on said sheet.

21. The surgical drape of claim 15, wherein said diverting feature is a plurality of channels being spaced apart and parallel to one another.

22. The surgical drape of claim 21, wherein all of said channels have the same width.

23. The surgical drape of claim 15, wherein said diverting feature being channels having an elongated portion and a narrow portion, the direction of said elongated portion being perpendicular to the direction of fluid flow on said sheet.

24. The surgical drape of claim 15, wherein said diverting feature being raised areas having an elongated portion and a narrow portion, the direction of said elongated portion being perpendicular to the direction of fluid flow on said sheet.

25. The surgical drape of claim 15, wherein said diverting feature is a plurality of channels each being located next to at least one of a plurality of raised sections.

26. A surgical drape for use during surgery on a patient, comprising a sheet configured for covering at least a portion of the patient during surgery, at least one diverting feature located on said sheet and having substantially the same fluid absorbent properties as a section of said sheet immediately adjacent to said diverting feature, said diverting feature configured for at least partially transferring fluid from one location on said sheet to another location on said sheet while absorbing at least a portion of the fluid;
  wherein said diverting feature is a plurality of channels each being located next to at least one of a plurality of raised sections; and
  further comprising a resilient material located between a fabric and said sheet, said resilient material being located in a void proximate to said raised section.

27. A surgical drape for use during surgery of a patient, comprising:
  a sheet configured for covering at least a portion of the patient during surgery, said sheet having an absorbent region; and
  a diverting feature being a plurality of parallel channels located on said absorbent region, the material forming said channels having substantially the same fluid absorbent properties as said absorbent region, said channels being integrally formed with said absorbent region, said channels having an elongated portion and a narrow portion wherein said channels having wicking properties in order to transfer fluid from one location on said absorbent region to another location on said absorbent region.

28. A method for forming a diverting feature in a surgical drape, comprising:
  positioning an absorbent region of a drape between an embossing plate and a resilient member;
  applying a force such that said embossing plate engages said absorbent region and at least a portion of said absorbent region is urged into said resilient member;
  heating said absorbent region while said absorbent region is being urged into said resilient member; and
  removing said absorbent region from said resilient member, a diverting feature being formed in said drape.

29. The method of claim 28, wherein said resilient member is a high temperature resistant rubber deformable foam.

30. The method of claim 28, further comprising:
  providing a fixed plate adjacent to said embossing plate;
  providing a base adjacent to said resilient member; and
  wherein said step of applying a force includes applying a force against said base such that said embossing plate and at least a portion of said absorbent region of said drape is urged into said resilient member.

31. The method of claim 28, wherein said absorbent region is heated to a temperature of at least 53.33° C., and said step of applying a force is a force of at least 137895 Pascals.

* * * * *